United States Patent
Schmidt

(10) Patent No.: US 6,495,718 B1
(45) Date of Patent: Dec. 17, 2002

(54) METHOD FOR SUPPRESSING SORBATE- AND/OR SORBIC ACID-INDUCED DISCOLORATION

(75) Inventor: Ralf Schmidt, Nuremberg (DE)

(73) Assignee: Nutrinova Nutrition Specialties & Food Ingredients GmbH, Frankfurt am Main (DE)

( * ) Notice: Subject to any disclaimer, the term of this patent is extended or adjusted under 35 U.S.C. 154(b) by 0 days.

(21) Appl. No.: 09/577,948

(22) Filed: May 25, 2000

(30) Foreign Application Priority Data

May 26, 1999 (DE) .......................... 199 23 838
Jun. 22, 1999 (DE) .......................... 199 28 495

(51) Int. Cl.$^7$ .................. C07C 57/10; A01N 43/16; A01N 25/00; A61K 39/385; A61K 6/00
(52) U.S. Cl. .................. 562/601; 514/451; 514/458; 514/813; 424/195.1; 424/401
(58) Field of Search .................. 424/195.11, 401; 514/813, 458, 451; 562/607

(56) References Cited

U.S. PATENT DOCUMENTS

| | | | |
|---|---|---|---|
| 2,866,817 A | | 12/1958 | Montagna et al. .......... 562/601 |
| 3,961,088 A | * | 6/1976 | Besand et al. ............. 426/262 |
| 4,208,434 A | * | 6/1980 | Iacobucci et al. .......... 426/250 |
| 4,530,844 A | * | 7/1985 | Smerbeck et al. .......... 514/458 |
| 5,080,901 A | * | 1/1992 | Hangay et al. ............ 424/195.1 |
| 5,122,381 A | * | 6/1992 | Nishimura et al. ......... 426/654 |
| 5,354,902 A | | 10/1994 | Merciadez et al. ......... 562/601 |
| 5,468,492 A | * | 11/1995 | Szaloki et al. ............ 424/195.1 |
| 5,539,129 A | * | 7/1996 | Zysman et al. ............. 549/430 |
| 5,834,513 A | * | 11/1998 | Ptchelintsev et al. ....... 514/561 |
| 5,883,137 A | * | 3/1999 | King ...................... 514/813 |
| 5,922,335 A | * | 7/1999 | Ptchelintsev ............. 424/401 |
| 5,945,409 A | * | 8/1999 | Crandall .................. 514/78 |
| 5,972,993 A | * | 10/1999 | Ptchelintsev ............. 514/449 |
| 5,977,184 A | * | 11/1999 | Birdsall et al. ........... 514/685 |

FOREIGN PATENT DOCUMENTS

| | | |
|---|---|---|
| DE | 195 04 999 | 8/1996 |
| EP | 0 595 576 A2 | 5/1994 |
| EP | 0 754 450 | 1/1997 |

OTHER PUBLICATIONS

Webster's II: New Riverside University Dictionary, The Riverside Publishing Company, 1994, p. 383.*
Chemical Abstracts, vol. 130, No. 16, Apr. 19, 1999, abstract No. 209022, A. Wei, R. Zhou: "Study on antioxidants from myrobalam" XP002148341.
Database WPI, Derwent Publications Ltd., AN 1990–302405, XP002148342, San–Ei Chem: "Anthocyanin stabilization using flavanol, water–soluble antioxidant and phosphate for food etc." Aug. 27, 1990.
Derwent Abstract of DE 195 04 999, 1996.
Domsch, A, "Die kosmitischen Präparate", Band 2, Wässrige und tensidhaltige Formulierungen, 4$^{th}$ Ed., pp. 328–331, Augsburg, Verlag für chemische Industrie (1994).
Arya, S.S., "Stability of Sorbic Acid in Aqueous Solutions", Journal Agric. Food Chem., vol. 28, pp. 1246–1249, (1980).
Arya, S.S. et al., "Degradation Products of Sorbic Acid in Aqueous Solutions", Food Chemistry vol. 29, pp. 41–49, (1988).
Ledward, D.A., "Stability of Sorbic Acid in Intermediate Moisture Systems", Food Additives and Contaminants, vol. 7, No. 5, pp. 677–683, (1990).
Thakur, B.R. et al., "Chemistry of Sorbates–A Basic Perspective", Food Reviews International, 10(1), pp. 71–91, (1994).

* cited by examiner

Primary Examiner—Michael G. Hartley
Assistant Examiner—Michael A. Willis
(74) Attorney, Agent, or Firm—Finnegan, Henderson, Farabow, Garrett & Dunner, L.L.P.

(57) ABSTRACT

Compositions which comprise sorbic acid and/or one or more sorbates, and a flavonoid and/or flavonoid derivative, a method for the preparation thereof, and their use.

11 Claims, No Drawings

METHOD FOR SUPPRESSING SORBATE- AND/OR SORBIC ACID-INDUCED DISCOLORATION

This application claims priority benefit under 35 U.S.C. § 119 of German patent application no. 199 23 838.3, filed on May 26, 1999, and German patent application no. 199 28 495.4, filed on Jun. 22, 1999. The contents of both priority documents are incorporated by reference herein.

FIELD OF THE INVENTION

The invention relates to sorbate-preserved compositions, to methods for their preparation, and to their use, in particular as color-stabilized cosmetic and pharmaceutical compositions.

Cosmetic compositions are substances or preparations comprising substances which are intended to be applied externally to the person or used in body cavities (e.g. in the oral cavity) for cleansing, care or for influencing the appearance or the body odor or for conveying odor impressions. Pharmaceutical compositions are substances or preparations comprising substances which are primarily intended to alleviate or to eliminate illnesses, suffering, bodily injuries or pathological complaints.

Cosmetic compositions are, for example, hair- and body-cleansing products, such as shampoos, shower gels or washing lotions, creams, lotions and gels for skincare and for protection against solar irradiation, oral hygiene and dental care products, decorative cosmetics, self-tanning compositions, water-, alcohol- or surfactant-containing cloths for cleansing or freshening and other products within the meaning of the definition given above.

For the purposes of this invention, pharmaceutical compositions are aqueous or alcohol-containing solutions, gels or emulsions comprising a water phase and a lipid phase which comprise pharmaceutically active substances. Examples are medicaments which are administrable orally, ointments, creams, eye drops or nasal drops, sprays, tinctures, injection solutions and more besides.

Typical ingredients of cosmetic and pharmaceutical compositions are water, surfactants and cosurfactants, oils, fats, waxes, emulsifiers, solubilizers, film formers, polymers, conditioning agents, bodying agents, thickeners, gel formers, dyes, pigments, pearlizing agents, fragrances, light protection filters, deodorant active ingredients, moisturizers, natural extracts such as herbs, plant extracts or essential oils, solvents, abrasive agents and more besides. In addition, very different active ingredients are used in such products, for example skin-smoothing, antiinflammatory, pain-relieving, antibacterial, antifungal and antiviral substances.

DESCRIPTION OF THE RELATED ART

Cosmetic and pharmaceutical compositions, in particular water-containing ones, or those which are able to absorb water as a result of the intake of water or atmospheric moisture, generally comprise one or more preservatives which protect the composition from attack by spoilage or pathogenic microorganisms during storage and during use.

Sorbic acid (2,4-hexadienoic acid) and its salts, in particular the readily water-soluble potassium salt, has been used throughout the world for many years for preserving foods, and cosmetic and pharmaceutical compositions. Sorbic acid is an unsaturated fatty acid which is notable for particular physiological compatibility. Sorbic acid is metabolized in the human body analogously to its fatty acid, does not accumulate and is classified as safe by the scientific advisory boards of the World Health Organization and of the European Union. The ADI value, which can be evaluated as a measure of the physiological acceptability of food additives, set by both panels for sorbic acid is 0 to 25 mg/kg of bodyweight per day and is therefore the highest ADI value by far of all preservatives. Sorbic acid and sorbates are considered to be nonallergenic and are therefore not mentioned in any of the known allergy databanks (e.g. Leatherhead Food Tolerance Databanks Project) either. With regard to using cosmetic compositions, the CIR expert panel of the CTFA classifies these preservatives as "safe" on the basis of the toxicological and allergological data known for sorbic acid and sorbates. Sorbic acid and sorbates have been approved throughout the world in the majority of countries for preserving cosmetic compositions.

The effectiveness of sorbic acid is directed primarily toward yeasts and molds, and toward numerous bacteria. The effectiveness of sorbic acid depends on the undissociated portion and therefore on the pH of the material to be preserved. Because of the high pK of 4.76, sorbic acid is also suitable for preserving weakly acidic materials (to pH 6.5), in contrast to other preservatives based on organic acids.

In solid form, sorbic acid and most sorbates, in particular potassium sorbate and calcium sorbate, are stable. In aqueous solution, in foods and in cosmetic compositions, sorbic acid, however, is subject to oxidative influences. Particularly as a result of oxidative cleavage of the double bonds, it is possible for aldehydes and ketones to form, which may be the cause of off-flavors. Polymerization products of these aldehydes can likewise be responsible for color changes, especially browning reactions, such as the reaction products of these aldehydes with amino acids or other primary or secondary amino groups. Products of this type are referred to as Maillard products and are often responsible for color changes in cosmetic compositions and foods.

Precisely in cosmetic compositions, for which significantly longer storage times have to be assumed than for most foods and which are subjected to oxidative influences, a sorbate-induced brown discoloration has been described (Domsch, A. (1994): Die kosmetischen Präparate, [Cosmetic Preparations], volume 2, wässrige und tensidhaltige Formulierungen [Aqueous and surfactant-containing formulations], 4th Edition, p. 329, Augsburg, Verlag für chemische Industrie).

The mechanism of the oxidation of sorbic acid and appropriate stabilization measures have often been the subject of scientific investigations (Arya, S. (1980): Stability of sorbic acid in aqueous solutions, Journal Agric. Food Chem. 28, 1246–1249; Arya, S., Thakur, B. (1988): Degradation products of sorbic acid in aqueous solutions, Food Chem. 29, 41–49; Ledward, D. (1990): Stability of sorbic acid in intermediate moisture systems, Food Add. Contam. 7, 677–683; Merciades, M., Mohammed, K., Maniere, F. (1992): Stabilized sorbic acid or salt thereof, EP-A 0 595 576; Thakur, B., Singh, R., Arya, S. (1994): Chemistry of sorbates—a basic perspective. Food Rev. Intern. 10, 71–91).

Since at least the first step of the reaction chain which later on leads to the formation of colored compounds is presumably an oxidative attack on one of the double bonds present in the sorbic acid molecule, the co-use of an antioxidative constituent appears necessary. It is, however, known that common antioxidants, such as, for example, propyl gallate or BHA (t-butylmethoxyphenol) which, because of their high antioxidative capacity, are customary in numerous cosmetic products and also in some foods, do not have a color-stabilizing action on sorbate-containing cosmetic or pharmaceutical formulations.

Within the framework of the above investigations, attempts were sometimes made to reduce the described sorbate-induced discolorations and odor changes of foods by adding metal ions (in particular manganese) in the concentration range from 0.1 to 5 ppm. However, metal ions only have an antioxidative effect in an extremely narrow dosage range. U.S. Pat. No. 5,354,902 describes the color stabilization of sorbate-containing aqueous systems using manganese ions. Overall, however, the addition of heavy metal ions to solve the discoloration problem does not appear to be very suitable since both toxic, and also ecologically unfavorable effects emanate from the heavy metals. Added to this is the fact that said heavy metals can, depending on the concentration chosen, also have a prooxidative effect.

U.S. Pat. No. 2,866,817 describes the stabilization of aqueous solutions of sorbic acid and its salts, in particular Na sorbate, using 0.0005 to 0.5% of glucono-delta-lactone. However, in combination with typical constituents of cosmetic compositions, such as, for example, protein hydrolyzates, ethanolamides or amidopropylbetaines, which additionally favor discoloration, this method does not lead to success. Furthermore, because of its limited solubility even in solid form, Na sorbate is of no significance as a preservative for foods, and cosmetic and pharmaceutical compositions.

The protective measure which has hitherto been carried out most frequently for preventing sorbate-induced discolorations is the co-use of complexing agents (e.g. EDTA (ethylenediaminetetraacetate) and citric acid or salts thereof) which slow the sorbate-induced discolorations by complexing metal ions which have a prooxidative action.

This measure is particularly advantageous in cases of contamination by traces of metal ions which have a prooxidative effect in the cosmetic product. Under unfavorable conditions (e.g. elevated temperatures or intensive daylight irradiation of the sorbate-containing product), however, discolorations arise even in the absence of such prooxidative factors, meaning that complexing agents alone are unable to offer sufficient protection.

DE-A 195 04 999 describes the use of allantoin with or without citric acid or a salt thereof for reducing sorbate-induced discolorations in cosmetics and foods. However, this solution has the disadvantage that the color-stabilizing action is insufficient in conjunction with a number of frequently used ingredients of cosmetic products. Those ingredients of particular importance in this context are those which contain residual contents of free amines as a result of their preparation, or themselves are molecules containing primary or secondary amino groups. Examples of ingredients which act disadvantageously in this manner are amidopropylbetaines, protein hydrolyzates or ethanolamides, and fatty acid esters thereof.

Particularly under intensive irradiation by daylight, the color-stabilizing principle of a sorbate-containing cosmetic or pharmaceutical formulation is subject to particular requirements, which can only be partially met solely by the use of allantoin in conjunction with citric acid and citrates. Although the discoloration of corresponding products is reduced by the addition of allantoin in conjunction with citric acid and citrates, it is still visible.

There therefore continues to be a need for color-stabilizing additives which are able to suppress sorbate-induced discolorations in cosmetic or pharmaceutical compositions, or to reduce them appreciably even under unfavorable conditions such as elevated light and thermal stress.

SUMMARY OF THE INVENTION

Effective color stabilization is surprisingly achieved by adding a flavonoid to the sorbate-containing compositions, in particular a flavone or flavonal, preferably a water-soluble 3- or 7-glycoside of a flavonal, particularly preferably rutin, the rutinoside of quercetin. The flavonoids according to the invention are usually of a vegetable origin.

DETAILED DESCRIPTION OF THE INVENTION

Flavonoids are themselves pale yellowish products which are used, for example, in natural dyeing. In the pharmaceutical field, a number of flavonoids or their glycosides are attributed with a protective action against diseases of the veins (biflavonoids, such as hesperidin and rutin) and of liver parenchyma (silybin), and also an improvement of the coronary circulation (hawthorn extract) and diuretic effects (birch leaf drugs) or spasmolytic effects (camomile drugs). (Rompp Lexikon Chemie, 10th edition, Thieme Verlag, Stuttgart, N.Y.).

For the purposes of this invention, glycosides are combinations of the flavonoids with mono- or oligosaccharides, consisting of the monomeric building blocks glucose, rhamnose, arabinose, galactose, xylose or other monosaccharides, on carbon atom 3 or 7 of the flavonoid, as frequently occur in indigenous types of fruit and tropical fruits:

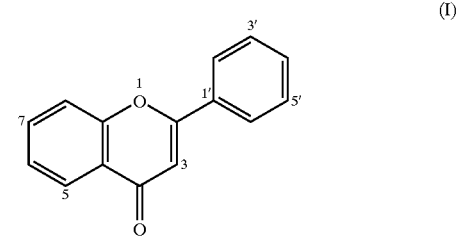

Formula (I) shows the basic structure of a flavone (3=H) or flavonal (3=OH, 4'=OH).

Examples of flavonoids which are effective according to the invention are the flavones apigenin (5=OH, 7=OH)

luteolin (5=OH, 7=OH, 3'=OH)

diosmetin (4'=OCH$_3$, 3'=OH)

chrysoeriol (3'=OCH$_3$, 4'=OH)

and the flavonals kaempferol (5=OH, 7=OH)

quercetin (5=OH,7=OH, 3'=OH)

morin (5=OH, 7=OH, 2'=OH)

robinetin (7=OH,3'=OH, 5'=OH)

gossypetin (5=OH, 7=OH,3'=OH,8=OH)

myricetin (5=OH, 7=OH, 3'=OH, 5'=OH)

fisetin (7=OH, 3'=OH)

isohamnetin (3'=OCH$_3$)

and the 3- and 7-glycosides thereof.

Because of their natural origin, all of these compounds have high acceptance as ingredients of cosmetic and pharmaceutical compositions and occur naturally in numerous types of berry fruits, citrus fruits and other types of fruit and vegetable and in some herbal plants.

The color-stabilizing action of these substances is surprising primarily because other representatives of the substance group of vegetable polyphenols either do not have a color-stabilizing effect on sorbate-preserved cosmetic or pharmaceutical compositions, or, under unfavorable conditions, such as, for example, intensive daylight irradiation, even lead to an acceleration of undesired discoloration reactions. Examples of compounds which do not have a stabilizing action on sorbate-containing cosmetic compositions are the large groups of hydroxycinnamic acids, hydroxycumaric acids and hydroxybenzoic acids and naturally occurring esters thereof with quinic acid, shikimic acid, malic acid, tartaric acid and myo-inositol. Some of these compounds even increase undesired discoloration.

Examples which may be mentioned here are ferulic acid and rosmarinic acid, which are frequently used in cosmetic compositions because of an antioxidative effect attributed to them, but do not show a positive effect with regard to the color stabilization of sorbate-containing products.

Synthetic antioxidants, such as propyl gallate or BHA, do not have a color-stabilizing action on sorbate-containing cosmetic or pharmaceutical formulations either.

All the more noteworthy is the differing behavior of flavonoid compounds and, in particular, of the 3-glycosides and 7-glycosides thereof.

While it is not the intention to express that the invention is limited to the activity mechanism described below, the following statement can nevertheless be assumed: The color-stabilizing action could firstly be explained by the relatively favorable solubility properties (better solubility in water as a result of the relatively large proportion of hydrophilic structures in the molecule), but also by a steric hindrance of oxidation or polymerization reactions at the phenolic groups of the molecule. Both are properties which antioxidative compounds do not necessarily have and whose absence is therefore in no way detrimental to their effectiveness in other systems, but to which, surprisingly, particular importance appears to be attributed for the present problem.

The flavonoid and/or its 3- or 7-glycoside are advantageously added to the composition, in particular the cosmetic or pharmaceutical composition, in a concentration of from 0.005 to 10% by weight, in particular 0.01 to 2% by weight, preferably 0.01 to 1 % by weight, particularly preferably 0.015 to 0.2% by weight, based on the total mass of the product. At the preferred use concentrations, flavonoids are themselves only very weakly color-imparting.

The sorbate-preserved compositions, in particular the cosmetic and pharmaceutical compositions, comprise between 0.005 and 5% by weight of sorbic acid or a salt thereof, in particular between 0.05 and 2% by weight, preferably between 0.1 and 0.8% by weight, particularly preferably between 0.15 and 0.4% by weight.

The invention is described in more detail below by reference to Examples:

A sorbate-preserved cosmetic model formulation (hair shampoo) without the addition of thickener was prepared according to the following basic recipe:

| | |
|---|---|
| Sodium lauryl myristyl ether sulfate (28%) | 22.4 g |
| Disodium laureth sulfosuccinate (40%) | 9.6 g |
| Cocamidopropylbetaine (30%) | 10.0 g |
| Polysorbate 20 (100%) | 1.6 g |
| Potassium sorbate | 0.5 g |
| Citric acid | 1.9 g |
| Triethanolamine | ad pH 5.0 |
| Aqua | ad 100 ml |

The product prepared in this way was mixed with a variety of additives in order to investigate their color-stabilizing action. To quantify the protective action of these additives from undesired product discolorations, the following test arrangement was used.

The product to be investigated was poured into a container open at the top and stored for 20–30 days under a strong light source (366 nm). The temperature of the product during storage was about 30° C. During this storage time, each of the products was repeatedly measured using a color-measuring instrument (Minolta Chromameter) for any discoloration. From the results, expressed in $\Delta E$, regression analysis was used to calculate the mean daily increase in the color value, which was given as the difference relative to the corresponding daily increases in the color value of a control sample (without additives). Thus, positive values indicate accelerated coloration of the model product, and negative values indicate reduced discoloration of the model product.

Specifically, the following results were obtained for the additives tested:

| | |
|---|---|
| Rutin (0.025%) | −0.19 |
| Comparative Example: | |
| Allantoin (0.5%) | −0.09 |
| Urea (5%) | 0.03 |
| Propyl gallate (0.05%) | 0.22 |
| BHA (0.02%) | 0.36 |
| Tocopheryl acetate (0.05%) | −0.02 |
| Ferulic acid (0.1%) | 0.02 |
| Rosmarinic acid (0.06%) | 0.11 |
| Phytic acid (0.1%) | 0.29 |
| EDTA (0.1%) | −0.12 |
| Iminodisuccinate, Na salt (0.1%) | 0 |
| Sodium hexametaphosphate (0.3%) | 0.06 |

From these results it is clear that rutin, as a representative of the substance class of glycosylated flavonoids, even in a concentration of 0.025% by weight, has a significant protective action toward the sorbate-dependent, light- and heat-induced discoloration of cosmetic compositions. This effect is clearly superior to the color-stabilizing effect of allantoin and that of EDTA. Other phenolic plant ingredients, such as ferulic acid or rosmarinic acid, show virtually no action, or even a discoloration-promoting action. Frequently used synthetic antioxidants such as BHA and propyl gallate likewise increase the tendency of the sorbate-preserved system toward discoloration instead of reducing it, as could be expected on the basis of their antioxidative potential.

I claim:

1. A method for suppressing sorbate- and/or sorbic acid-induced brown discoloration in a sorbate- and/or sorbic acid-preserved composition, which comprises adding an effective amount of a flavonoid to the composition.

2. A method as claimed in claim 1, wherein the composition comprises a sodium, potassium or calcium sorbate.

3. A method as claimed in claim 1, wherein the flavonoid is a compound of the formula (I)

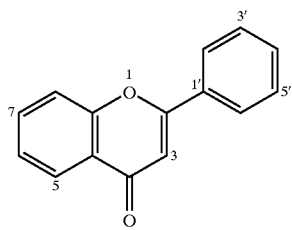

(I)

wherein 3=H, or wherein 3=OH and 4'=OH.

4. A method as claimed in claim 3, wherein the flavonoid is a compound of the formula (I) having the following substituents:

where 3=H,
- apigenin (5=OH, 7=OH),
- luteolin (5=OH, 7=OH, 3'=OH),
- diosmetin (4'=OCH$_3$, 3'=OH), or
- chrysoeriol (3'=OCH$_3$, 4'=OH); or where 3=OH and 4'=OH,
- kaempferol (5=OH, 7=OH),
- quercetin (5=OH, 7=OH, 3'=OH),
- morin (5=OH, 7=OH, 2'=OH),
- robinetin (7=OH, 3'=OH, 5'=OH),
- gossypetin (5=OH, 7=OH, 3'=OH, 8=OH),
- myricetin (5=OH, 7=OH, 3'=OH, 5'=OH),
- fisetin (7=OH, 3'=OH), or
- isohamnetin (3'=OCH$_3$), or a 3- or 7-glycoside thereof.

5. A method as claimed in claim 1, wherein the flavonoid is present in an amount of from 0.005 to 10% by weight, based on the weight of the composition.

6. A method as claimed in claim 1, wherein the sorbate and/or sorbic acid is present in an amount of from 0.005 to 5% by weight, based on the weight of the composition.

7. A method as claimed in claim 1, wherein the composition is a pharmaceutical composition.

8. A method as claimed in claim 1, wherein the composition is a cosmetic composition.

9. A method as claimed in claim 1, wherein the weight of the sorbate- and/or sorbic acid in the composition is greater than or equal to the weight of the flavonoid added to the composition.

10. A method as claimed in claim 1, wherein the weight of the sorbate- and/or sorbic acid in the composition ranges from 0.05 to 2% and the weight of the flavonoid added to the composition ranges from 0.01 to 2%.

11. A method as claimed in claim 9, wherein the weight of the sorbate- and/or sorbic acid in the composition ranges from 0.15 to 0.4% and the weight of the flavonoid added to the composition ranges from 0.015 to 0.2%.

* * * * *